(12) United States Patent
Wang et al.

(10) Patent No.: US 11,022,545 B2
(45) Date of Patent: Jun. 1, 2021

(54) MULTI-SPECTRAL GAS ANALYZER SYSTEM WITH MULTIPLE SETS OF SPECTRAL SENSITIVITY

(71) Applicant: Konica Minolta Laboratory U.S.A., Inc., San Mateo, CA (US)

(72) Inventors: Leiming Wang, Foster City, CA (US); Po-Chieh Hung, Cupertino, CA (US)

(73) Assignee: Konica Minolta Business Solutions U.S.A., Inc., San Mateo, CA (US)

( * ) Notice: Subject to any disclaimer, the term of this patent is extended or adjusted under 35 U.S.C. 154(b) by 792 days.

(21) Appl. No.: 15/176,480

(22) Filed: Jun. 8, 2016

(65) Prior Publication Data

US 2017/0045443 A1  Feb. 16, 2017

Related U.S. Application Data

(60) Provisional application No. 62/203,296, filed on Aug. 10, 2015.

(51) Int. Cl.

| | |
|---|---|
| *G01N 21/3504* | (2014.01) |
| *G01J 3/42* | (2006.01) |
| *G01N 33/00* | (2006.01) |
| *G01N 33/22* | (2006.01) |
| *G01J 3/02* | (2006.01) |
| *G01J 3/36* | (2006.01) |
| *G01J 3/12* | (2006.01) |
| *G01J 3/28* | (2006.01) |
| *G01N 33/24* | (2006.01) |

(52) U.S. Cl.
CPC .......... *G01N 21/3504* (2013.01); *G01J 3/42* (2013.01); *G01N 33/0063* (2013.01); *G01N 33/225* (2013.01); *G01J 3/0264* (2013.01); *G01J 3/36* (2013.01); *G01J 2003/1239* (2013.01); *G01J 2003/2826* (2013.01); *G01J 2003/2836* (2013.01); *G01N 33/0047* (2013.01); *G01N 33/241* (2013.01); *G01N 2201/124* (2013.01); *G01N 2201/1247* (2013.01)

(58) Field of Classification Search
USPC ....................................... 250/339.01, 339.13
See application file for complete search history.

(56) References Cited

U.S. PATENT DOCUMENTS

| | | |
|---|---|---|
| 8,184,293 B2 | 5/2012 | Bonyuet et al. |
| 8,452,134 B1 | 5/2013 | Davids et al. |
| 2002/0036266 A1 | 3/2002 | Dreyer et al. |

(Continued)

OTHER PUBLICATIONS

N. Neumann et al.; "Tunable infrared detector with integrated micromachined Fabry-Perot filter"; J. Micro/Nanolith. MEMS MOEMS, vol. 7, No. 2, pp. 1-9; Apr.-Jun. 2008 (9 pages).

(Continued)

*Primary Examiner* — David P Porta
*Assistant Examiner* — Carolyn Fin
(74) *Attorney, Agent, or Firm* — Osha Bergman Watanabe & Burton LLP

(57) ABSTRACT

A system and method for multi-spectral gas concentration analysis that includes using a library of multiple sets of optimized spectral sensitivities prepared in advance, and a multi-spectral IR gas analyzer tuned to a set of optimized spectral sensitivity. The multi-spectral IR gas analyzer measures spectral absorption of gas using one or more different sets of optimized spectral sensitivities.

13 Claims, 13 Drawing Sheets

(56) References Cited

U.S. PATENT DOCUMENTS

2011/0184624 A1\* 7/2011 Han .................. F23N 5/082
                                                    701/101
2012/0170114 A1   7/2012 Domash et al.

OTHER PUBLICATIONS

J. K. Sell et al.; "Monitoring of Gas Mixtures by Means of a Flexible IR-Sensor System Utilizing Tunable Filters"; Elsevier, Procedia Engineering, vol. 47, pp. 285-288; 2012 (4 pages).

M. Stevenson et al.; "IR Emitting Quantum Dots for Defense Applications"; Proc. of SPIE, vol. 8720, pp. 1-10; 2013 (10 pages).

\* cited by examiner

MULTI-SPECTRAL GAS ANALYZER SYSTEM WITH MULTIPLE SETS OF SPECTRAL SENSITIVITY

BACKGROUND

Infrared (IR) absorption has applications in identifying components in a mixed gas system. Spectroscopic measurement methods such as Fourier transform spectroscopy (FTIR) and tunable filter spectroscopy (TFS) are required to measure gas compositions in a gas mixture when the absorbance spectra of the gas compositions overlap with each other. On the other hand, some multi-spectral type measurement may also be used to measure gas compositions in a gas mixture. In contrast to FTIR or TFS which measures the IR absorbance spectrum of the sample, a multi-spectral method may measure the IR absorption over several discrete wavelength bands.

SUMMARY OF THE INVENTION

Figure 1:
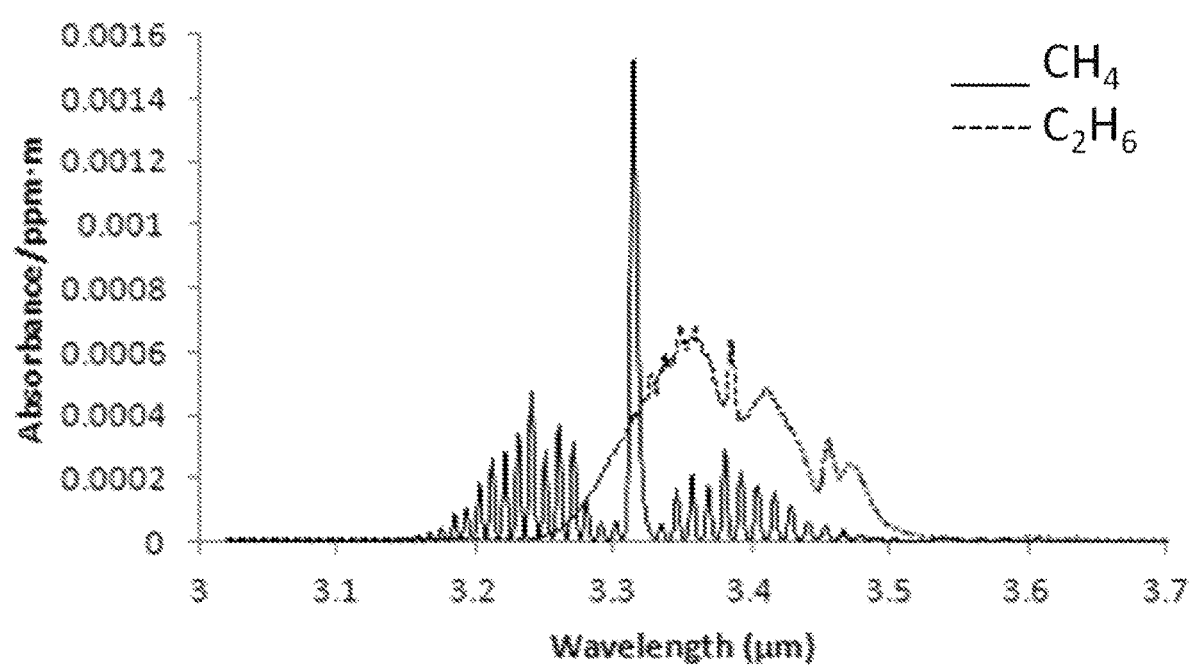
FIG. 1 shows a graph of absorbance in accordance with one or more embodiments of the invention.

In one aspect, embodiments of the invention relate to a method for multi-spectral gas concentration analysis that includes preparing a library of multiple sets of optimized spectral sensitivities, and measuring the spectral absorption of a gas using a multi-spectral IR gas analyzer tuned to one set of the multiple sets of optimized spectral sensitivities. The method includes comparing the multiple sets of optimized spectral sensitivities based on the signal level measured by the multi-spectral IR gas analyzer.

In another aspect, embodiments of the invention relate to a system for multi-spectral gas concentration analysis that includes a library of multiple sets of optimized spectral sensitivities prepared in advance and a multi-spectral IR gas analyzer tuned to a set of optimized spectral sensitivity. The multi-spectral IR gas analyzer measures spectral absorption of gas using one or more different sets of optimized spectral sensitivities.

Other aspects and advantages of the invention will be apparent from the following description and the appended claims.

DETAILED DESCRIPTION

Specific embodiments of the invention will now be described in detail with reference to the accompanying figures. Like elements in the various figures are denoted by like reference numerals for consistency. Further, the use of "Fig." in the drawings is equivalent to the use of the term "Figure" in the description.

In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

In general, embodiments of the invention relate to a multi-spectral gas analyzer method and system capable of composition measurement of gas mixtures where the possible concentrations may vary over a large range.

In contrast to techniques which measure an IR absorbance spectrum of the sample, a multi-spectral method may measure the IR absorption over one or more discrete wavelength bands, resulting in a faster, more energy-efficient process. For each wavelength band the measured signal may be integrated over the bandwidth of the wavelength band. Because of the broadband integrated nature of the detection, the measurement accuracy of multi-spectral analysis is dependent on spectral sensitivity of the multi-spectral system. For example, the center wavelength, the bandwidth, and the peak amplitude of each of the one or more wavelength bands of the spectral sensitivity may all contribute to the measurement accuracy.

One or more embodiments of the invention determine an optimal spectral sensitivity (i.e., collection of wavelength bands) to accurately determine the concentrations of specific gases in a gas mixture. The optimal spectral sensitivity in a multi-spectral gas analyzer system is dependent on the specific gas concentrations and absorption of the specific gases. For example, in a gas with a high concentration, or a mixture of gases, the transmission at a main absorption wavelength region may be very low. A low transmission may result in a poor signal-to-noise ratio for that particular wavelength range.

In one or more embodiments of the invention, multiple sets of spectral sensitivity are prepared for different ranges of gas concentrations. The multiple spectral sensitivity sets may contain at least one set in which the multiple wavelength bands all overlap with the major absorption peaks of the species to be analyzed, and at least one set in which at least one wavelength band is outside or only partially overlapping the major absorption peaks of the species to be analyzed. The stored multiple sets of spectral sensitivity sets may then be used to evaluate the concentrations of gas mixtures in accordance with one or more embodiments of the invention.

One or more embodiments of the invention may be combined with additional concentration sensors to select the optimal set of spectral sensitivity based on the concentration of the gases, and improve the accuracy and speed of evaluating the concentrations of mixed gas sample.

FIG. 1 shows a graph of absorbance in accordance with one or more embodiments of the invention. FIG. 1 demonstrates the simulated absorbance spectra of methane ($CH_4$) and ethane ($C_2H_6$) in the 3.0-3.7 µm wavelength range. As known, the absorbance spectra of methane and ethane have characteristic absorption peaks, the most predominate being in the 3.3-3.4 µm wavelength vicinity.

FIGS. 2 and 3 demonstrate simulation results showing the significant effect that the spectral sensitivity has on the accuracy of multispectral analysis of gas mixtures in accordance with embodiments of the invention.

Figure 2A:
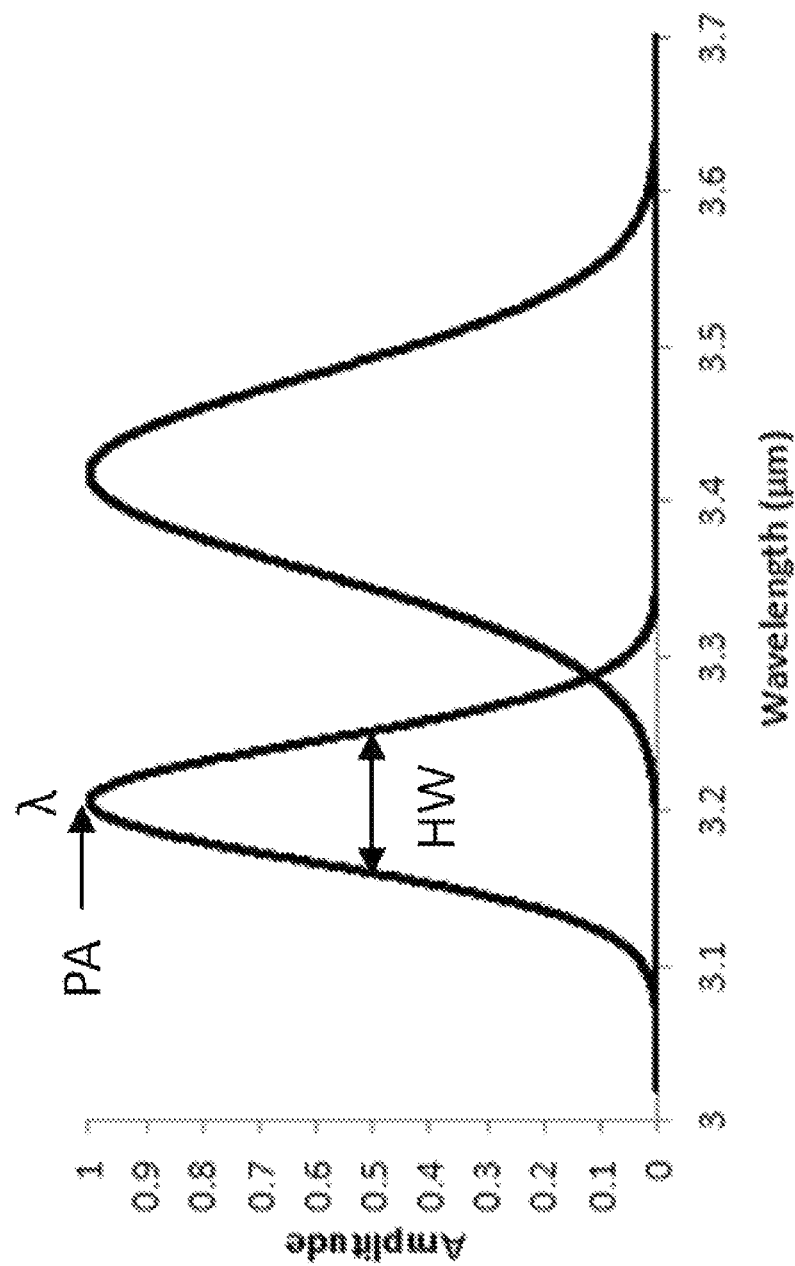
FIG. 2A shows a set of spectral sensitivities in accordance with one or more embodiments of the invention.

FIG. 2A shows a set of spectral sensitivities in accordance with one or more embodiments of the invention. FIG. 2A demonstrates a set of spectral sensitivities that contains two spectral bands used in a multispectral IR gas analyzer system. Although, FIG. 2A shows a set of spectral sensitivities containing two spectral bands, embodiments of the invention are not limited to two bands. In one or more embodiments of the invention, the number of bands may be selected based on the number of different components, or gases, contained in the mixed gas. For example, the number of spectral bands may be equal to, greater than, or less than the number of different gases in the gas mixture.

In accordance with one or more embodiments of the invention, the spectral sensitivity may be characterized by three parameters for each wavelength band: the center-wavelength ($\lambda$), the full width at half maximum, or simply half width (HW), and the relative peak amplitude (PA) of the wavelength band.

Figure 2B:
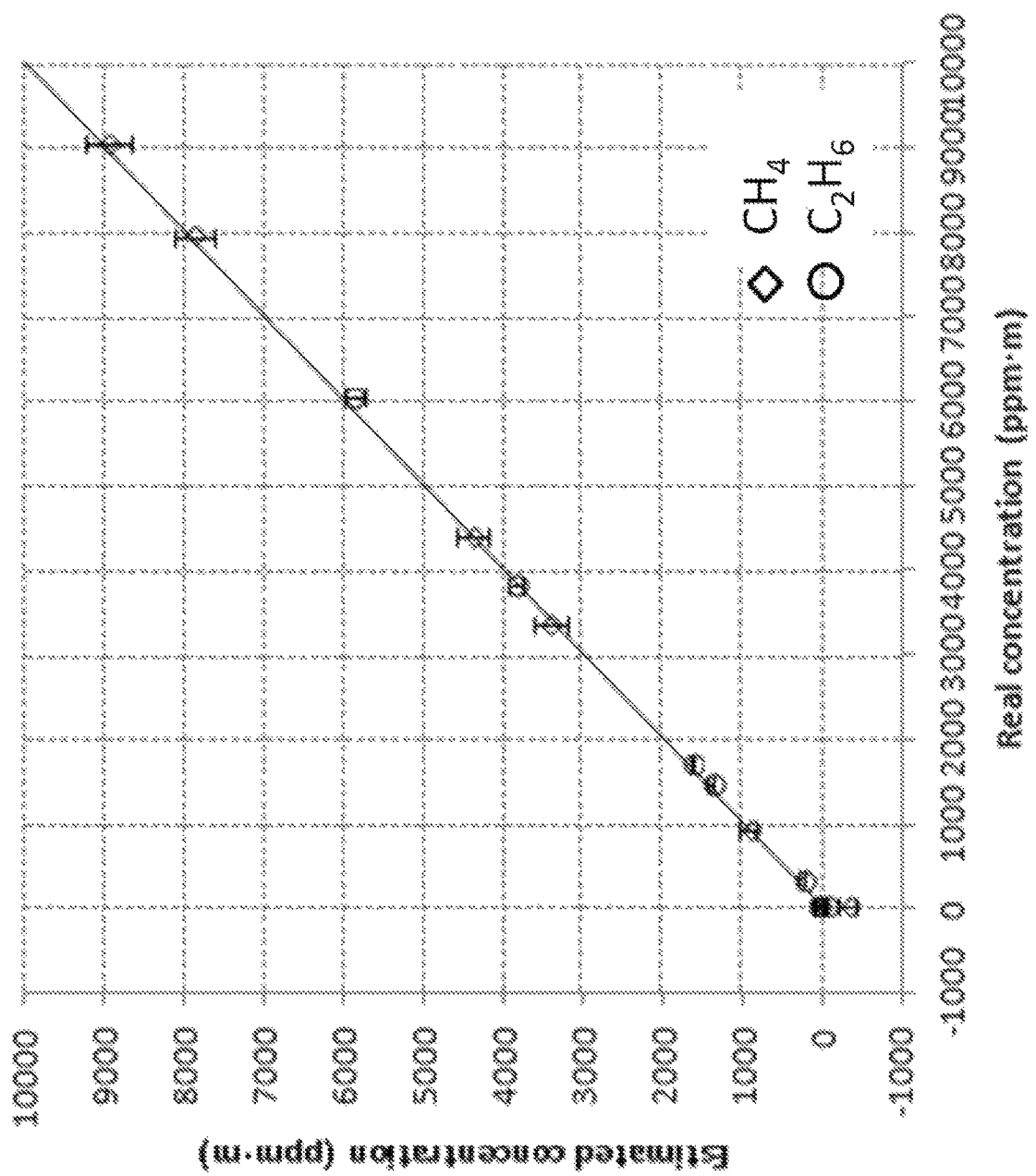
FIG. 2B shows estimated concentration in accordance with one or more embodiments of the invention.

FIG. 2B shows estimated concentration in accordance with one or more embodiments of the invention, based on the spectral sensitivities shown in FIG. 2A. FIG. 2B demonstrates the simulated results for the spectral sensitivity set shown in FIG. 2A in accordance with one or more embodiments of the invention. FIG. 2B plots the simulated detection concentration of each of the gas species Vs. the real concentration of each of the gas species.

Figure 3A:
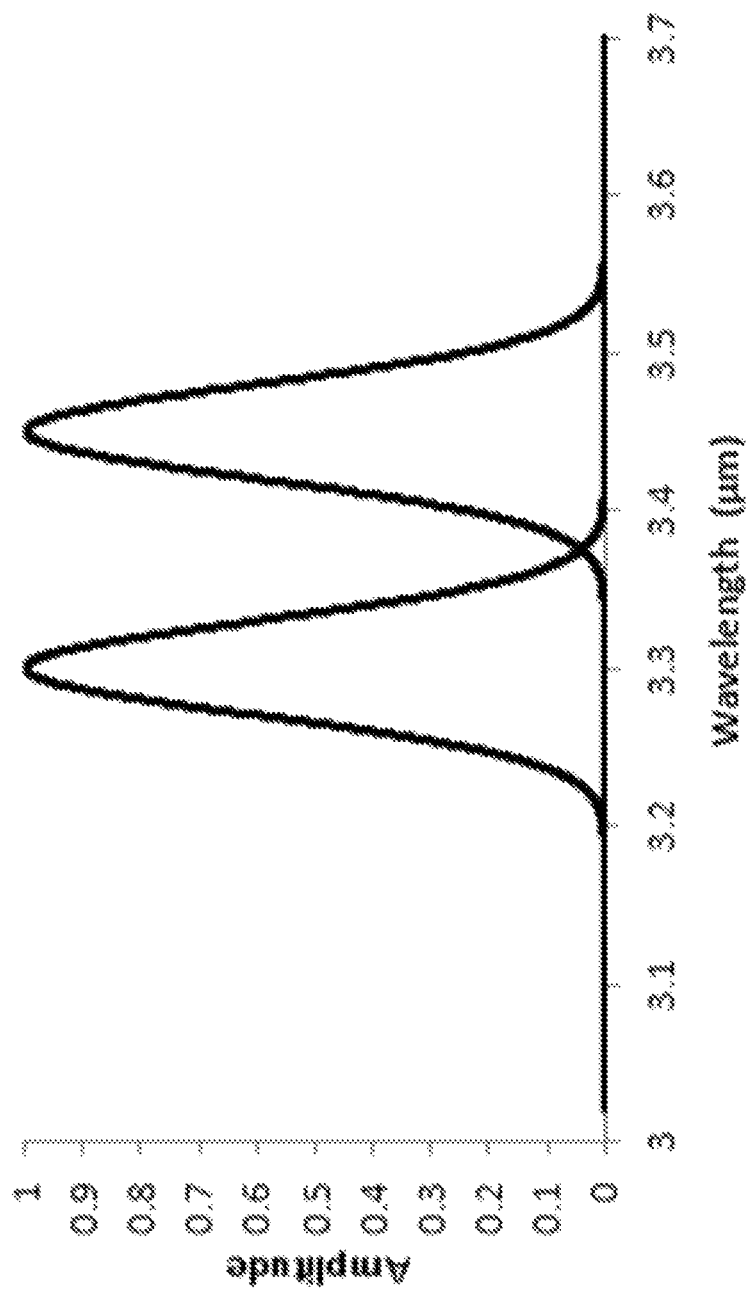
FIG. 3A shows a set of spectral sensitivities in accordance with one or more embodiments of the invention.
Figure 3B:
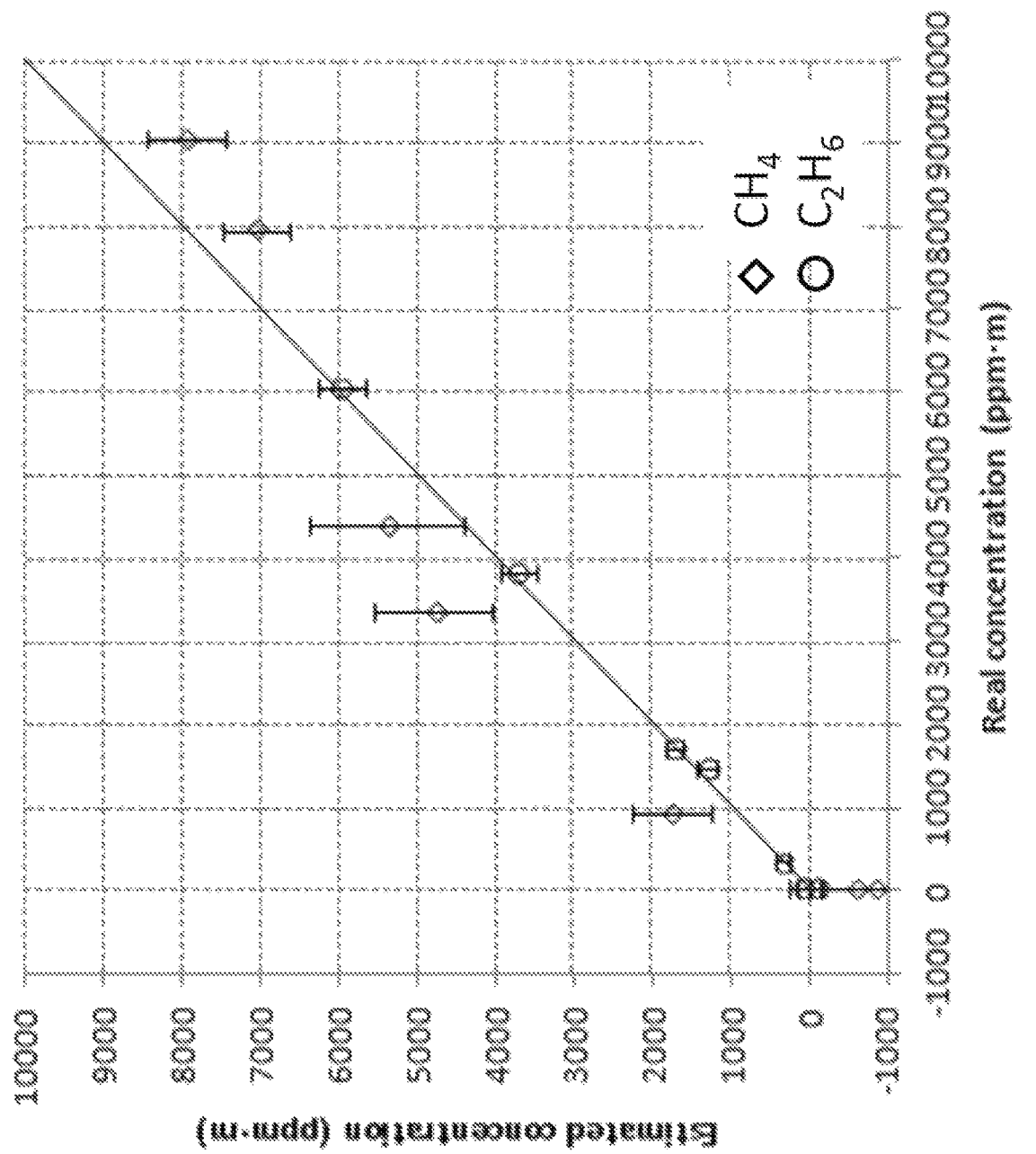
FIG. 3B shows estimated concentration in accordance with one or more embodiments of the invention.

FIGS. 3A and 3B demonstrate how the selection of spectral sensitivity set may influence the results of the concentration analysis. FIG. 3A shows a spectral sensitivity set (different than that illustrated in FIG. 2A) used in the gas mixture demonstrated by FIG. 1 in accordance with one or more embodiments of the invention. FIG. 3B plots the simulated detection concentration of each of the gas species Vs. the real concentration of each of the gas species for the spectral sensitivity set shown in FIG. 3A.

In one or more embodiments of the invention, the spectral sensitivity set may be selected based on the absorption peaks of one or more of the individual gases in the gas mixture, or the absorption of the combined gas mixture. As shown FIGS. 3A and 3B, the error may be greater if the spectral sensitivity set is selected to have center-wavelength ($\lambda$) and half width (HW) that is different from that of the optimal spectral sensitivity set as shown in FIG. 2A. In accordance with one or more embodiments of the invention, as demonstrated in FIGS. 2A and 2B, the spectral sensitivity set may be selected to be off peak, relative to the absorption of the gases in the gas mixture. As one of ordinary skill in the art would know, the magnitude of the absorption depends on the concentration. Therefore, for higher concentrations, one or more of the embodiments of the invention may select spectral sensitivities with wavelength bands that are off peak, while lower concentrations may select spectral sensitivities with wavelength bands on peak absorptions.

Figure 4A:
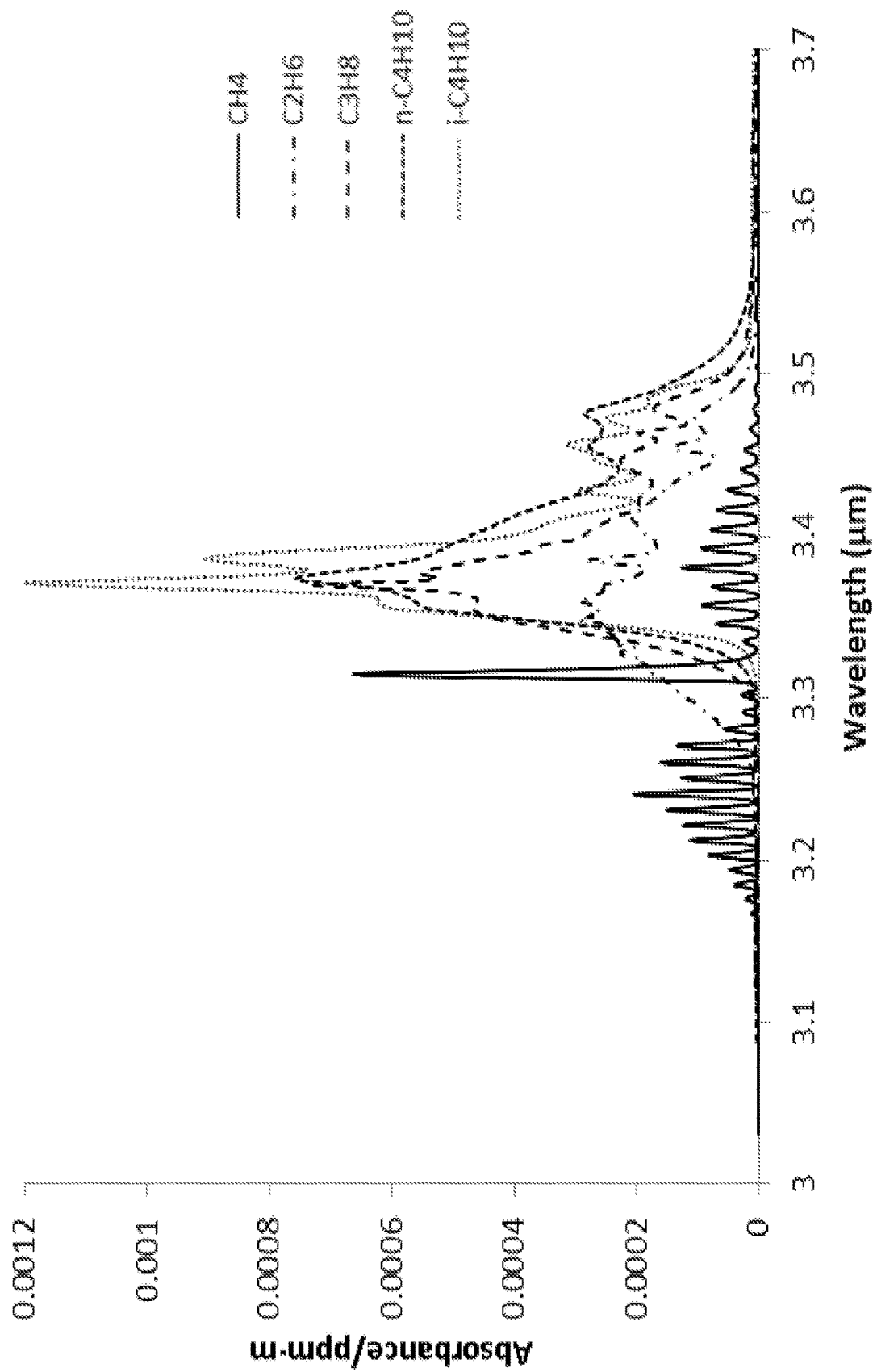
FIG. 4A shows a graph of absorbance in accordance with one or more embodiments of the invention.
Figure 4B:
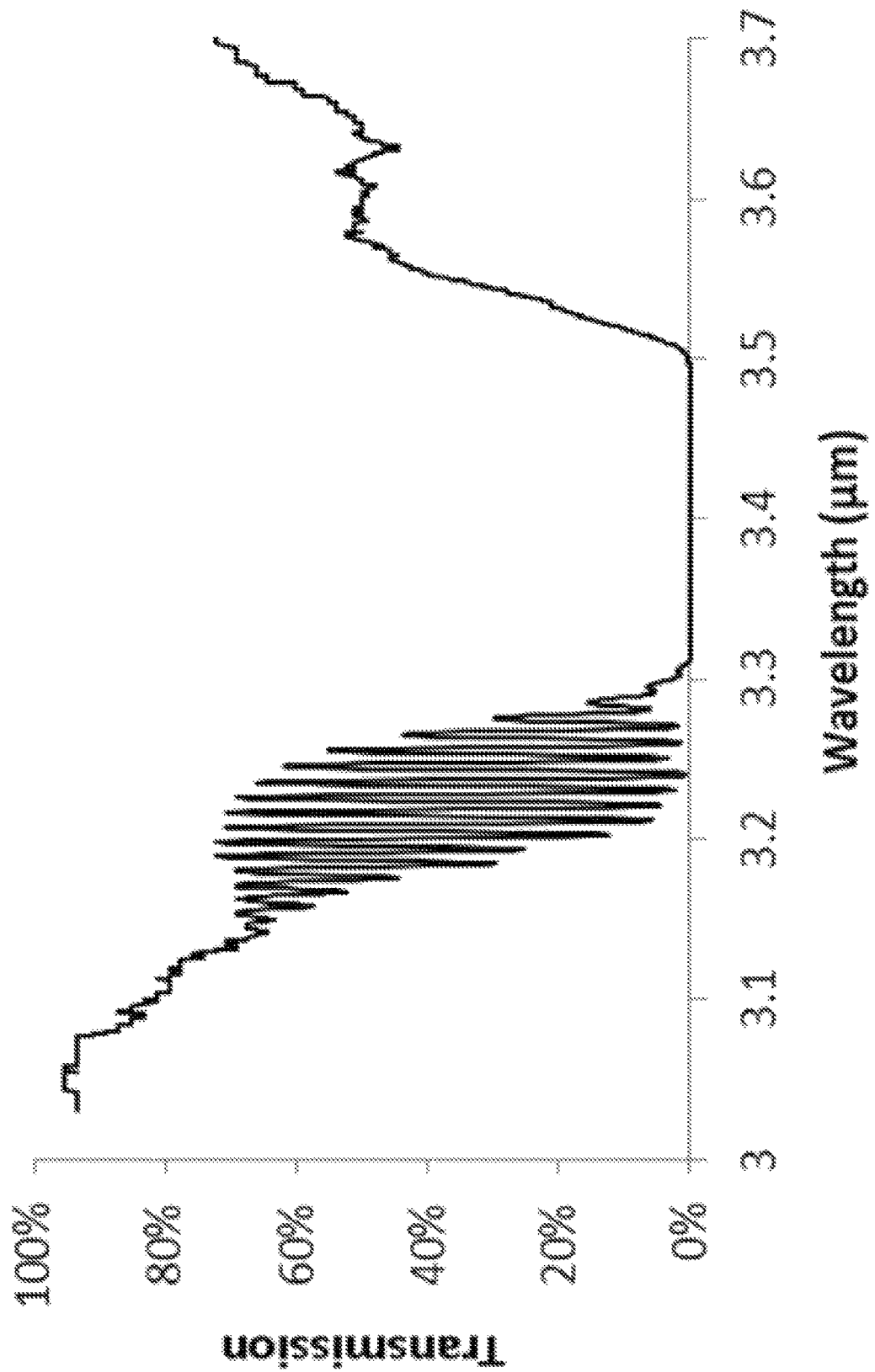
FIG. 4B shows a graph of transmittance in accordance with one or more embodiments of the invention.

FIG. 4A demonstrates an absorbance spectra of five hydrocarbon gases, methane ($CH_4$), ethane ($C_2H_6$), propane ($C_3H_8$), butane ($n-C_4H_{10}$) and i-butane ($i-C_4H_{10}$) in accordance with one or more embodiments of the invention. FIG. 4B shows an IR transmission spectrum through a 1 meter path of the five gas mixture, assuming the mixture contains $10^4$ ppm concentration of each gas. As shown in FIG. 4B, for this demonstrated example concentration of the gas mixture, the IR light is nearly completely absorbed over the 1 meter path, resulting in very low transmission at ~3.3-3.5 µm wavelength range. Therefore, spectral sensitivities tuned to the ~3.3-3.5 µm wavelength range will be unable to accurately analyze the gas concentration.

Figure 5A:
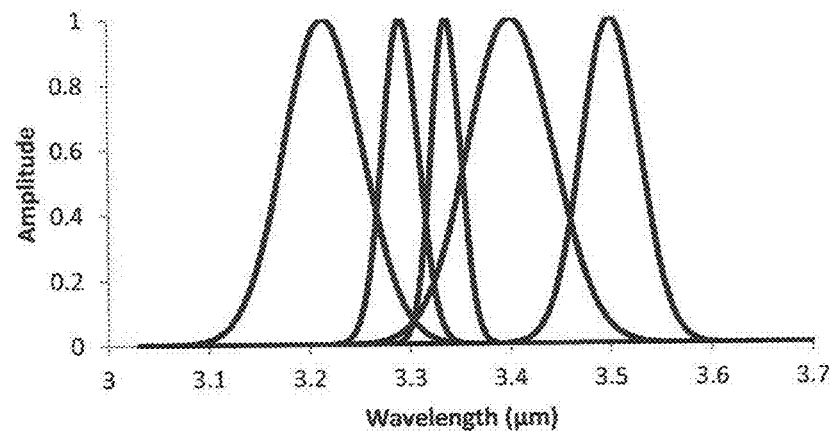
FIG. 5A shows a set of spectral sensitivities in accordance with one or more embodiments of the invention.
Figure 5B:
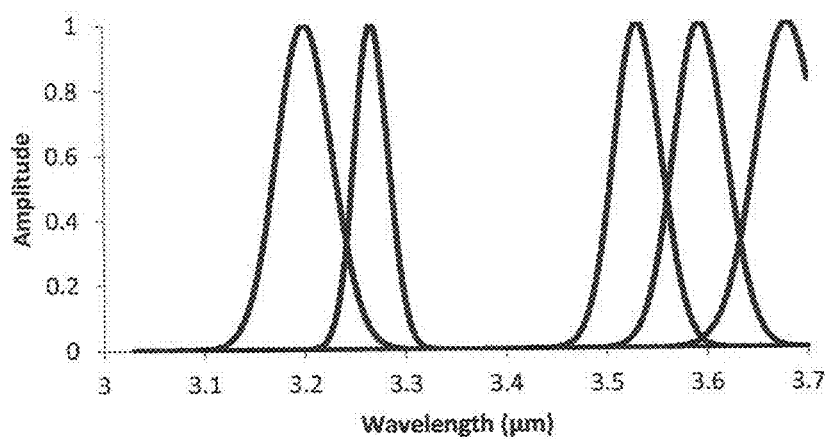
FIG. 5B shows a set of spectral sensitivities in accordance with one or more embodiments of the invention.

FIGS. 5A and 5B demonstrate optimized spectral sensitivity sets for different concentrations in accordance with one or more embodiments of the invention. FIG. 5A is the optimized spectral sensitivities for 5-band multispectral compositional concentration measurement of the five gas mixture (as shown in FIG. 4A) with a total concentration of less than 6,000 ppm·m. FIG. 5B is the optimized spectral sensitivities for 5-band multispectral compositional concentration measurement of the five gas mixture (as shown in FIG. 4A) with a total concentration of greater than or equal to 50,000 ppm·m. As demonstrated in FIG. 5B, for high gas concentrations, spectral positions outside the main absorption peaks of the gases may be optimal in accordance with one or more embodiments of the invention. FIGS. 5A and 5B demonstrate the need for different sets of spectral sensitivities for measuring gas mixtures when the possible concentrations may span a large range in accordance with one or more embodiments of the invention.

Figure 6:
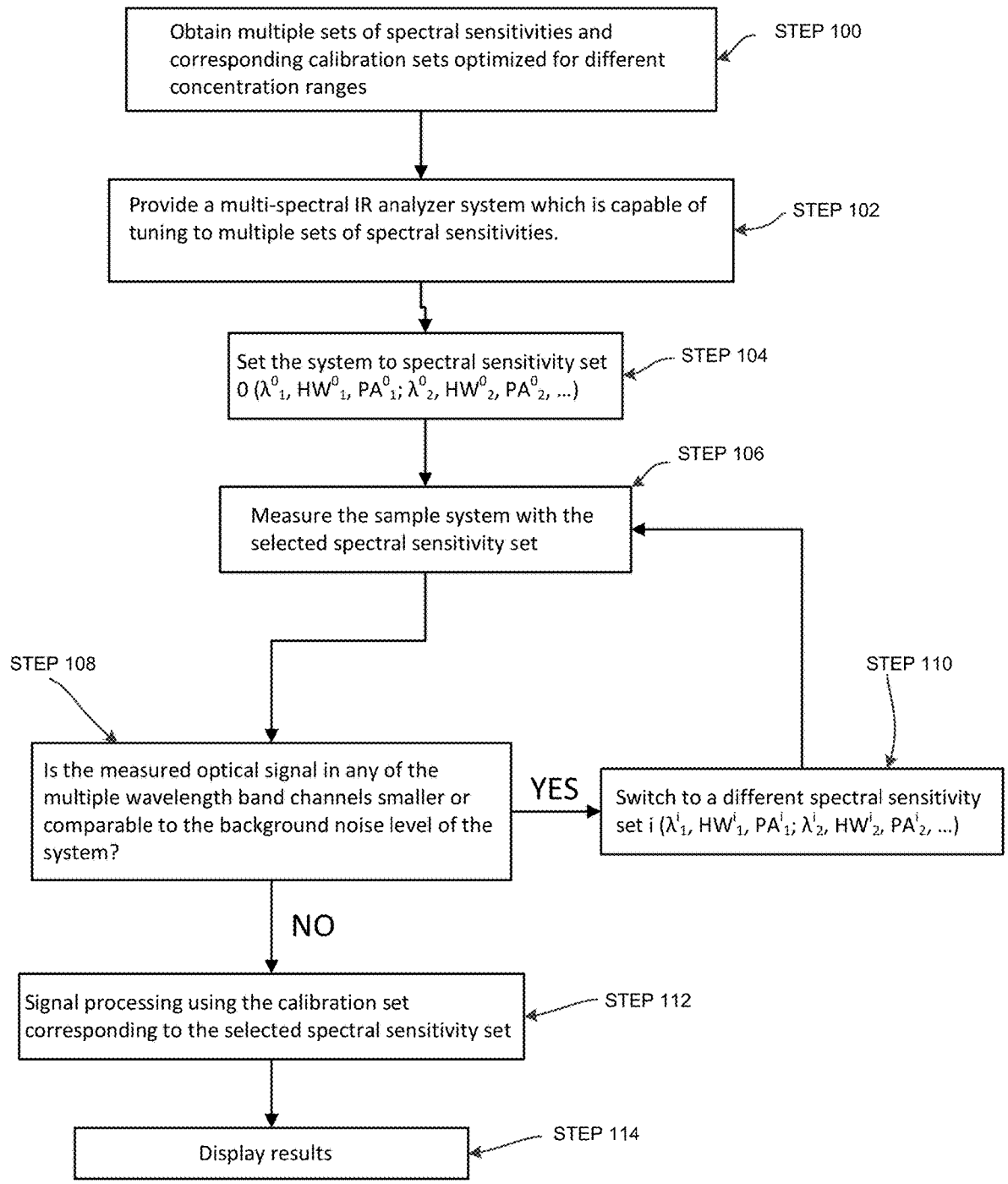
FIG. 6 shows a flowchart in accordance with one or more embodiments of the invention.

FIG. 6 is a flow chart in accordance with one or more embodiments of the invention. In Step 100, a library of multiple sets of spectral sensitivities and corresponding calibration sets optimized for different concentration ranges are obtained. Optimization of spectral sensitivity and calibration set for each concentration range may be obtained using method known in the arts such as least squares method. The calibration sets may contain factors associated with specific instruments, in order to quantitatively compare the different absorption measurements. The multiple spectral sensitivity sets may contain at least one set in which the multiple wavelength bands all overlap with the major absorption peaks of the species to be analyzed. Further, the multiple spectral sensitivity sets may contain at least one set in which at least one wavelength band is outside or only partially overlapping the major absorption peaks of the species to be analyzed.

In one or more embodiments of the invention, at a low concentration, the multiple spectral sensitivity set in which the multiple wavelength bands all overlap with the major absorption peaks of the species to be analyzed may be denoted as Set 0. For higher concentrations, the multiple spectral sensitivity set in which at least one wavelength band is outside or only partially overlapping the major absorption peaks of the species to be analyzed may be denoted as Set 1.

In Step 102, a multi-spectral gas analyzer system that is capable of tuning or selecting the multiple sets of spectral sensitivities is provided to perform the measurements associated with the multiple sets of spectral sensitivities. The multi-spectral gas analyzer system may measure the absorption over the predetermined wavelength bands and may include multiple sets of calibration coefficients corresponding to the multiple spectral sensitivity sets saved in a chip integrated in the system in accordance with one or more embodiments of the invention. Embodiments of the multispectral gas analyzers may include multiple IR detectors combined with a filter wheel, an IR focal plane array with different filter integrated in front of each pixel, or an array of IR sources with predesigned emission spectrum, or combinations thereof.

In Step 104, the initial spectral sensitivity set is selected. In one or more embodiments of the invention, if the concentration is unknown, the initial spectral sensitivity set may be the set denoted as Set 0, described above. In Step 106, the sample absorption is measured with the initial spectral sensitivity set. In Step 108, the measured optical signal in any of the wavelength bands of the spectral sensitivity set is evaluated and compared to a pre-defined level. If the measured optical signal in any of the wavelength bands is smaller than, or equal to the pre-defined level, the process proceeds to Step 110, where a different spectral sensitivity set is selected, and Steps 106 and 108 are repeated in accordance with one or more embodiments of the invention.

If the measured optical signal in any of the wavelength bands is greater than the pre-defined level, the process proceeds to Step 112, where the measurement results are processed and accepted. In Step 114, the results of the concentration analysis are displayed.

Alternatively, Steps 106 and 110 may be repeated for all of the different spectral sensitivity sets without inserting the decision by the step 108, and after measuring by all of the different spectral sensitivity sets, one of the measuring results that have the measured optical signal in any of the wavelength bands is greater than the pre-defined level may be chosen for the display in Step 114.

In one or more embodiments, if the measured optical signal in any of the multiple wavelength band channels is smaller or comparable to the background noise level of the system, a new spectral sensitivity set may be selected. In addition, or alternatively, a predetermined threshold of the signal-to-noise ratio may be established. Therefore, if the signal-to-noise ratio is smaller than the predetermined threshold, a new spectral sensitivity set may be selected in accordance with one or more embodiments of the invention.

In one or more embodiments of the invention, if the concentration is unknown, the process may begin with the spectral sensitivity set denoted as Set 0, described above. In one or more embodiments of the invention, multiple measurements with different spectral sensitivity sets may be combined to improve overall accuracy. The use of multiple spectral sensitivity sets may be advantageous for mid-range concentrations. In one or more embodiments, two or more sets of spectral sensitivity may be used.

One or more embodiments of the invention may be combined with additional gas concentration sensors. In one or more embodiments of the invention, selection of the spectral sensitivity set may be based on the concentration of the gases measured by the additional gas concentration sensors.

Figure 7:
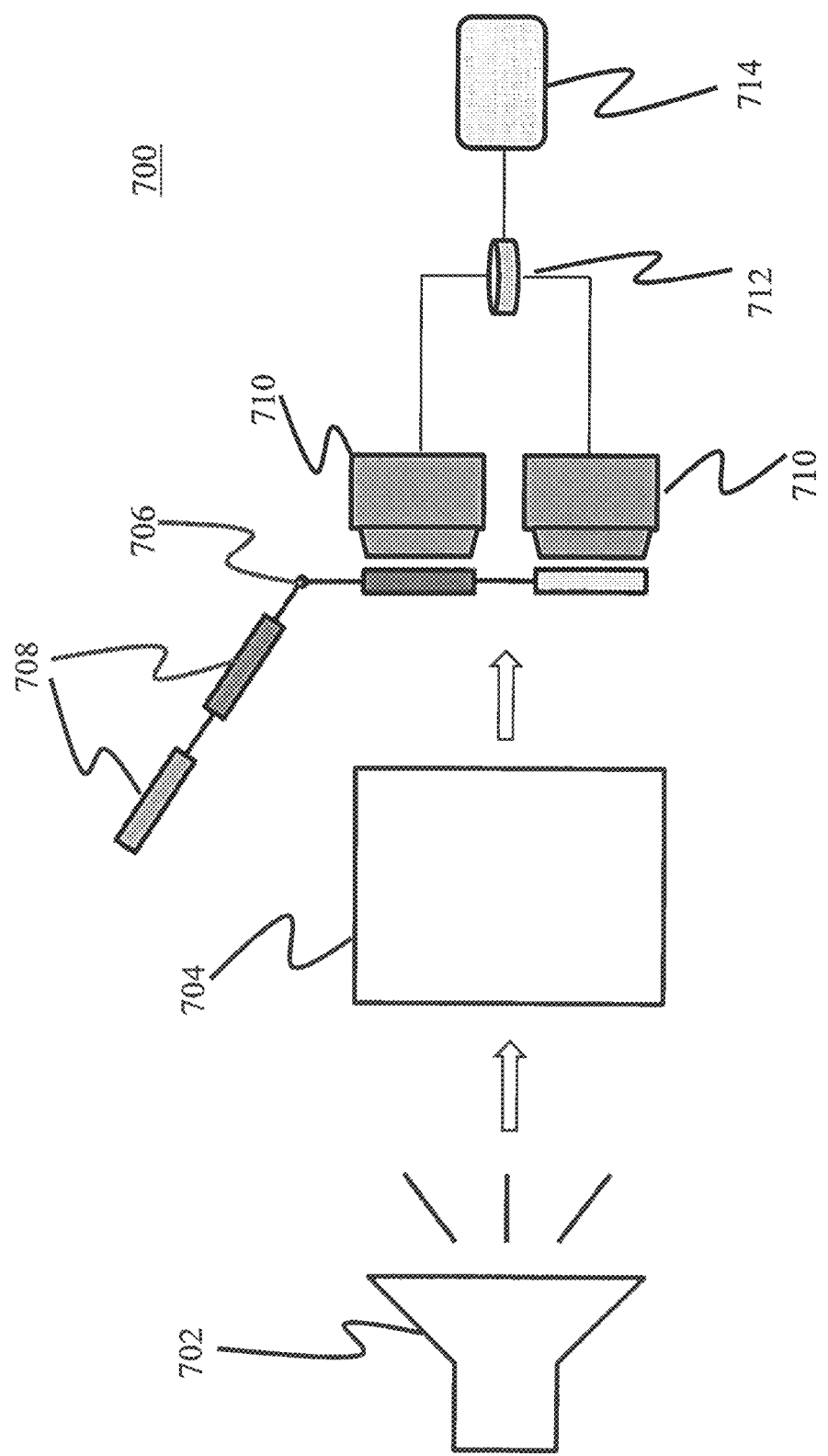
FIG. 7 shows a schematic in accordance with one or more embodiments of the invention.

FIG. 7 demonstrates an example of a multi-spectral IR gas analyzer device with the capability of tuning to or selecting multiple sets of predetermined spectral sensitivities in accordance with one or more embodiments of the invention. The multi-spectral IR gas analyzer device (700) demonstrated in FIG. 7 includes a broad band IR source (702). The broad band IR source (702) may be any IR emitters or IR emitting lamps known in the art. In one or more embodiments, an ambient light source may be used as the IR source (702).

The device (700) also includes a sample cell (704) for collecting the gas mixtures. One of ordinary skill in the art will appreciate that the sample cell may have a fixed, or known, path length for the transmission of IR radiation. Alternatively, one or more embodiments of the invention may be used to detect the concentration or composition of gases in an open area.

The device (700) also includes a filter wheel (706) containing two or more sets of filters (708). The filters (708) may be selected based on the wavelength bands of the spectral selectivity sets. Examples of the filters include, but are not limited to, a Fabry-Perot filter (as demonstrated in Norbert Neumann, et al, "Tunable Infrared Detector with Integrated Micromachined Fabry-Perot Filter", Journal of Micro/Nanolithography, MEMS, and MOEMS, 2008, 7(2), 021004) or a Metamaterial filter (as demonstrated in U.S. Patent Publication No. 2012/0170114).

The device (700) also includes two or more broadband IR detectors (710), where the number of IR detectors coincides with the number of filters (708) on each arm of the filter wheel (706). A chip (712) is connected to the IR detectors (710) for data collection and signal processing. The chip (712) may include the multiple spectral sensitivity data sets corresponding to those of the filters (708) and the corresponding calibration data. The device (700) may also include a display (714) connected to the chip (712) for displaying measurement results.

Figure 8:
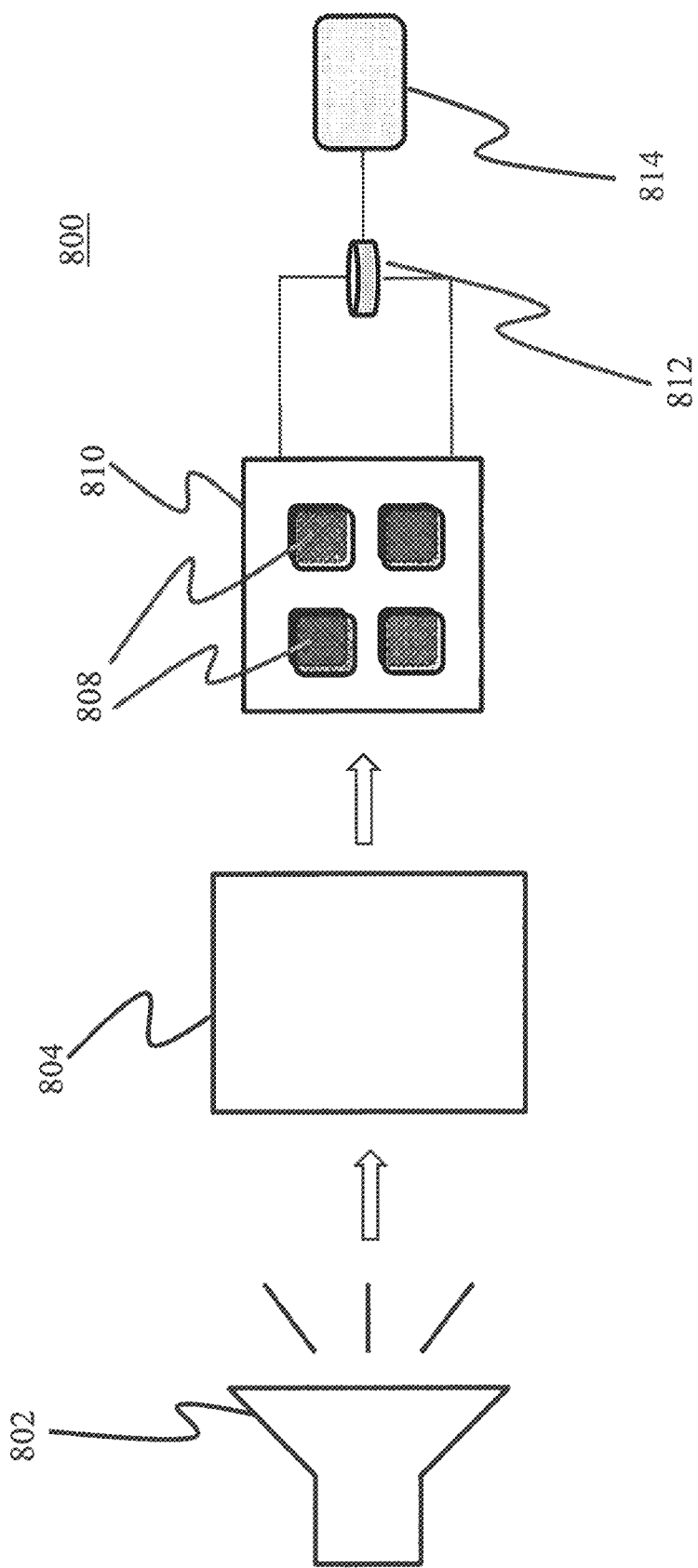
FIG. 8 shows a schematic in accordance with one or more embodiments of the invention.

FIG. 8 is another example of a multi-spectral IR gas analyzer device (800) in accordance with one or more embodiments of the invention. Similarly to the example of FIG. 7, the device (800) of FIG. 8 includes an IR source (802) and a sample cell (804). The device (800) includes an IR focal plane array (810) with filters (808) integrated on each pixel of the focal plane array. The device (800) also includes a chip (812) and display (814) as described above with respect to FIG. 7. The filters (808) are selected with respect to the wavelength bands of the predetermined spectral sensitivities set in accordance with one or more embodiments of the invention. In addition, the chip (812) may control the selection of different pixel combinations (spectral sensitivity sets) for data collection and signal processing in accordance with one or more embodiments of the invention. Examples of the IR focal plane array (810) with filters (808) include, but are not limited to, Fabry-Perot filter integrated IR imager or a plasmonic based frequency selective infrared sensors (for example, as demonstrated in U.S. Pat. No. 8,452,134).

Figure 9:
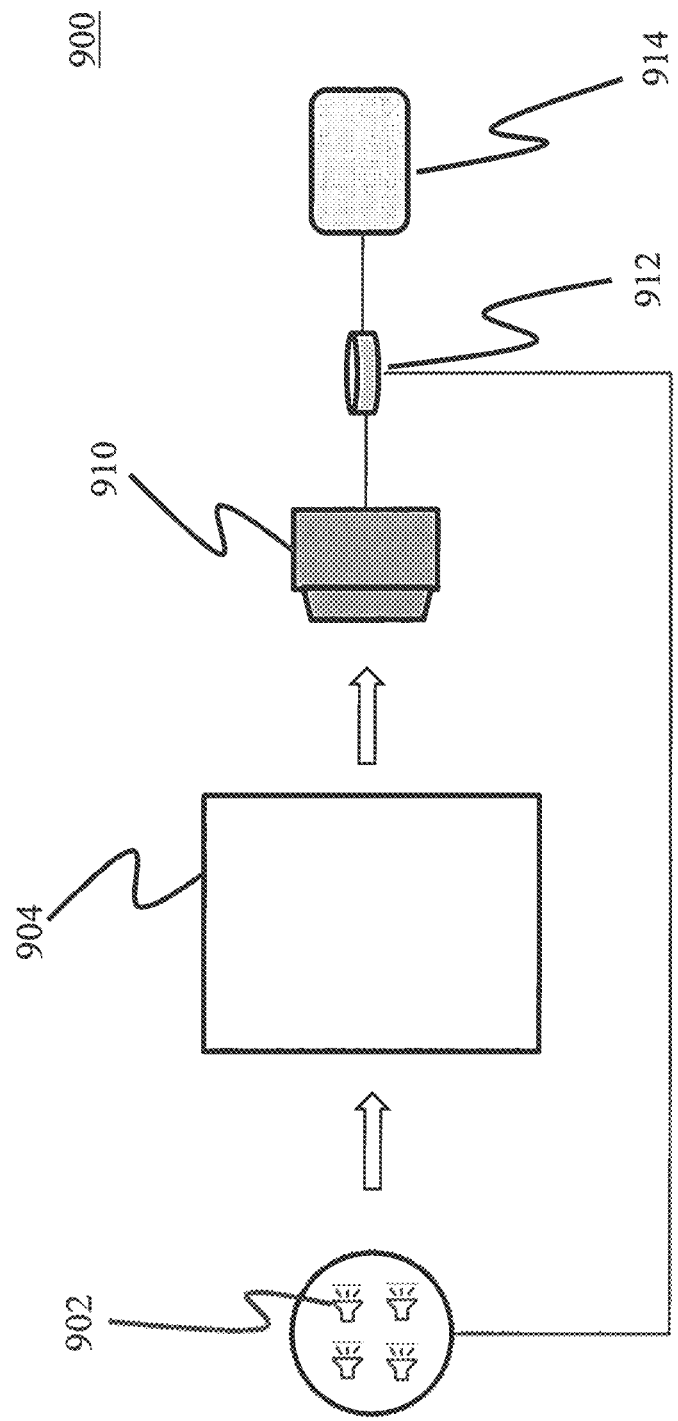
FIG. 9 shows a schematic in accordance with one or more embodiments of the invention.

FIG. 9 is another example of a multi-spectral IR gas analyzer device (900) in accordance with one or more embodiments of the invention. The device (900) includes an array of IR sources (902) with each IR source having a narrow predesigned emission spectrum. The emission spectra are selected with respect to the wavelength bands of the predetermined spectral sensitivities set in accordance with one or more embodiments of the invention. Examples of such IR sources include, but are not limited to, tunable diode lasers, quantum cascade lasers, or IR emitting quantum dots (for example, as described in M. Stevenson, et al, "IR emitting quantum dots for defense applications", Proc. SPIE 8720, Photonic Application for Aerospace, Commercial, and Harsh Environments IV, 872017 (May 31, 2013)).

The device (900) also includes a sample cell (904) for collecting the gas mixtures, similar to the examples shown in FIGS. 7 and 8. In one or more embodiments of the invention, the system may be used for detecting gases in open area as well, without the sample cell (904). The device (900) includes a broadband IR detector (910).

The device (900) also includes a chip (912) connected to the IR detector (910) for data collection and signal processing in accordance with one or more embodiments of the invention. The chip (912) contains the multiple spectral sensitivity data sets where the wavelength ranges correspond to the output of the IR sources (902) and any corresponding calibration data. The chip (912) additionally may control which IR source (902) in the array is to be activated. In one or more embodiments of the invention, the device (900) may be controlled to perform the multi-spectral measurement in a sequential time manner. In other words, the chip (912) may control the IR sources (902) to perform measurements in one wavelength band at a time. The device (900) also may include a display (914) connected to the chip for displaying measurement results in accordance with one or more embodiments of the invention.

Figure 10:
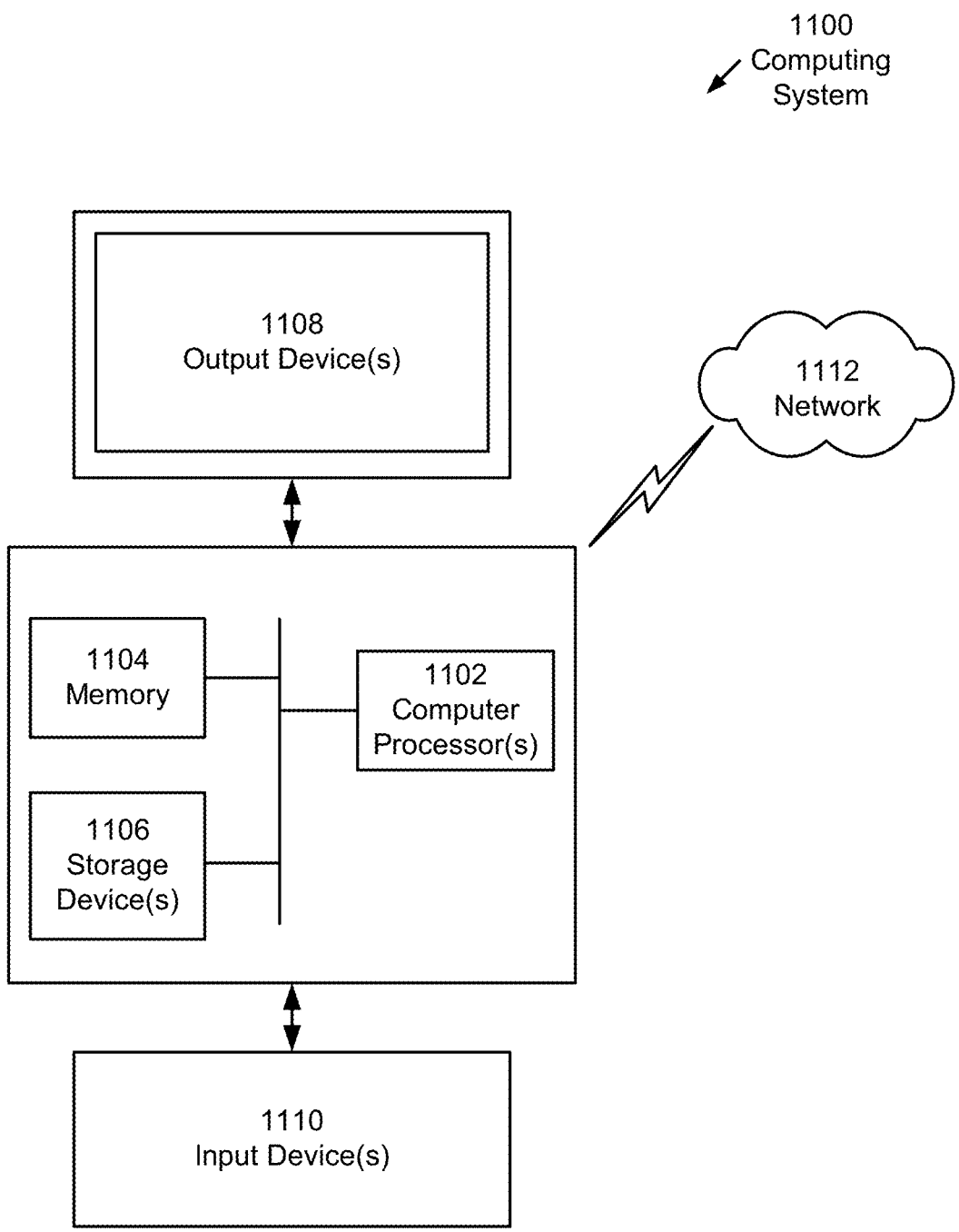
FIG. 10 shows a schematic of a computer system in accordance with one or more embodiments of the invention.

In one or more embodiments of the invention, the multi-spectral gas analyzer system chip may include a computer. The analysis of the spectral data may be analyzed on virtually any type of computer regardless of the platform being used. For example, as shown in FIG. 10, a computer system 1100 includes one or more processor(s) 1102 (such as a central processing unit (CPU), integrated circuit, etc.), associated memory 1104 (e.g., random access memory (RAM), cache memory, flash memory, etc.), a storage device 1106 (e.g., a hard disk, a solid state memory drive (SSD), an optical drive such as a compact disk drive or digital video disk (DVD) drive, a flash memory stick, etc.), and numerous other elements and functionalities typical of today's computers (not shown). The computer system 1100 may also include input means 1110, such as a keyboard, a mouse, a microphone, or data acquisition devices (not shown). Further, the computer system 1100 may include output means, such as a monitor 1108 (e.g., a liquid crystal display (LCD), a plasma display, or cathode ray tube (CRT) monitor) that may function as the display shown in FIGS. 7-9 in accordance with one or more embodiments of the invention. The computer system 1100 may be connected to a network 1112 (e.g., a local area network (LAN), a wide area network (WAN) such as the Internet, or any other type of network) via a network interface connection (not shown). Those skilled in the art will appreciate that many different types of computer systems exist, and the aforementioned input and output means may take other forms. For example, spectral selectivity calibration data sets may be stored on a server at remote location to easily maintain the data. Generally speaking, the computer system 1100 includes at least the minimal processing, input, and/or output means necessary to practice embodiments of the invention.

Further, software instructions in the form of computer readable program code to perform embodiments of the invention may be stored, temporarily or permanently, on a tangible computer readable storage medium, such as a compact disc (CD), a diskette, a solid state memory device (SSD), a tape, memory, or any other non-transitory tangible computer readable storage device.

In addition, one or more embodiments of the invention may be realized in an embedded computer system. Further, one or more embodiments of the invention may be realized in an erasable programmable read only memory (EPROM), programmable logic device (PLD) or in another hardware solutions.

Embodiments of the invention may advantageously provide a gas sensing system for a large range of gas concentrations. Embodiments of the invention may advantageously provide a system for measuring gases where concentration is unknown low or high. In one or more embodiments of the invention, off-peak spectral sensitivity is used to avoid small signal output for high gas concentration.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for multi-spectral gas concentration analysis, the method comprising:
  preparing a library of multiple sets of spectral sensitivities;
  measuring a first spectral absorption of a gas using a multi-spectral IR gas analyzer tuned to a first set of the multiple sets of spectral sensitivities;
  comparing a signal level of the first measured spectral absorption of the gas by the multi-spectral IR gas analyzer to a predetermined threshold;
  switching the multi-spectral IR gas analyzer to a second set of the multiple sets of spectral sensitivities; and
  measuring a second spectral absorption of the gas using the second set of the multiple sets of spectral sensitivities, wherein
  the first set of the multiple sets of spectral sensitivities is for a first gas concentration;
  the second set of the multiple sets of spectral sensitivities is for a second gas concentration; and
  the second gas concentration is higher than the first gas concentration.

2. The method of claim 1, wherein
  in the switching of the multi-spectral IR gas analyzer to the second set of the multiple sets of spectral sensitivities, the second set of the multiple sets of spectral sensitivities is selected based on a gas concentration of the gas measured by a gas concentration sensor included in the multi-spectral IR gas analyzer.

3. The method of claim 1, wherein
  in the switching of the multi-spectral IR gas analyzer to the second set of the multiple sets of spectral sensitivities, the second set of the multiple sets of spectral sensitivities is selected based on a location of absorption peaks of the first measured spectral absorption of the gas relative to one or more wavelength bands in the multiple sets of spectral sensitivities.

4. The method of claim 1, wherein the multiple spectral sensitivity sets contain at least one set in which multiple wavelength bands overlap with absorption peaks of the gas.

5. The method of claim 1, wherein the multiple spectral sensitivity sets contain at least one set in which at least one wavelength band partially overlaps absorption peaks of the gas.

6. The method of claim 1, wherein the multiple spectral sensitivity sets contain at least one set in which at least one wavelength band does not overlap absorption peaks of the gas.

7. A system for multi-spectral gas concentration analysis, the system comprising:
  a library of multiple sets of spectral sensitivities prepared in advance of a spectral absorption measurement;
  a multi-spectral IR gas analyzer configured to:
    measure a first spectral absorption of a gas using a first set of the multiple sets of spectral sensitivities;
    compare a measured signal level of the first measured spectral absorption of the gas to a predetermined threshold;
    output a measuring result of the first measured spectral absorption of the gas in response to the measured signal level being greater than the predetermined threshold;

switch to a second set of the multiple sets of spectral sensitivities in response to the measured signal level being less than or equal to the predetermined threshold; and measure a second spectral absorption of the gas using the second set in response to the measured signal level being less than or equal to the predetermined threshold.

8. The system of claim 7, wherein the multi-spectral IR gas analyzer is configured to switch to the second set of the multiple sets of spectral sensitivities based on a gas concentration of the gas measured by a gas concentration sensor included in the multi-spectral IR gas analyzer.

9. The system of claim 7, wherein the multi-spectral IR gas analyzer is configured to select the second set of the multiple sets of spectral sensitivities based on a location of absorption peaks of the first measured spectral absorption of the gas relative to one or more wavelength bands in the multiple sets of spectral sensitivities.

10. The system of claim 7, wherein
the first set of the multiple sets of spectral sensitivities is for a first gas concentration,
the second set of the multiple sets of spectral sensitivities is for a second gas concentration, and
the second gas concentration is higher than the first concentration.

11. The system of claim 7, wherein the multiple spectral sensitivity sets contain at least one set in which multiple wavelength bands overlap with absorption peaks of the gas.

12. The system of claim 7, wherein the multiple spectral sensitivity sets contain at least one set in which at least one wavelength band partially overlaps absorption peaks of the gas.

13. The system of claim 7, wherein the multiple spectral sensitivity sets contain at least one set in which at least one wavelength band does not overlap absorption peaks of the gas.

* * * * *